United States Patent
Malenfant et al.

(10) Patent No.: US 8,277,649 B2
(45) Date of Patent: Oct. 2, 2012

(54) MEMBRANES AND ASSOCIATED METHODS FOR PURIFICATION OF ANTIBODIES

(75) Inventors: Patrick Roland Lucien Malenfant, Clifton Park, NY (US); Cathryn Ellen Olsen, Gansevoort, NY (US); Vincent Francis Pizzi, Millis, MA (US); Gary William Yeager, Rexford, NY (US); Robert Scott Duthie, Schenectady, NY (US); Per Ola Lind, Uppsala (SE); Stina Elisabeth Hallgren, Uppsala (SE); Annika Morrison, Uppsala (SE)

(73) Assignee: General Electric Company, Niskayuna, NY (US)

( * ) Notice: Subject to any disclaimer, the term of this patent is extended or adjusted under 35 U.S.C. 154(b) by 431 days.

(21) Appl. No.: 12/636,833

(22) Filed: Dec. 14, 2009

(65) Prior Publication Data
US 2011/0139717 A1   Jun. 16, 2011

(51) Int. Cl.
*B01D 15/08* (2006.01)
(52) U.S. Cl. ............... 210/198.2; 210/502.1; 210/635; 210/656
(58) Field of Classification Search ............ 210/635, 210/656, 658, 659, 198.2, 502.1; 521/25, 521/32
See application file for complete search history.

(56) References Cited

U.S. PATENT DOCUMENTS

| | | | |
|---|---|---|---|
| 4,699,717 A * | 10/1987 | Riesner et al. | 536/25.4 |
| 5,110,875 A | 5/1992 | Jaxa-Chamiec et al. | |
| 5,350,523 A * | 9/1994 | Tomoi et al. | 210/683 |
| 6,103,117 A | 8/2000 | Shimagaki et al. | |
| 6,359,113 B1 * | 3/2002 | Ramage et al. | 530/335 |
| 6,881,761 B2 * | 4/2005 | Kotsuka et al. | 521/32 |
| 7,385,040 B2 | 6/2008 | Johansson et al. | |
| 7,465,397 B2 | 12/2008 | Siwak et al. | |
| 2007/0102363 A1 * | 5/2007 | Little et al. | 210/656 |
| 2007/0244307 A1 | 10/2007 | Engstrand et al. | |
| 2007/0259453 A1 | 11/2007 | Engstrand et al. | |
| 2008/0014625 A1 | 1/2008 | Etzel | |
| 2009/0035552 A1 | 2/2009 | Childs et al. | |
| 2011/0068002 A1 * | 3/2011 | Lin et al. | 204/296 |

FOREIGN PATENT DOCUMENTS

| | | |
|---|---|---|
| EP | 2060316 A1 | 5/2009 |
| WO | 2004076485 A1 | 9/2004 |
| WO | 2006043895 A1 | 4/2006 |
| WO | 2008086335 A2 | 7/2008 |
| WO | 2009007451 A1 | 1/2009 |

OTHER PUBLICATIONS

Dharmesh M Kanani, Elena Komkova, Tiffany Wong, Alicja Mika, Ronald F Childs and Raja Ghosh; "Separation of human plasma proteins HSA and HIgG using high-capacity macroporous gel-filled membranes"; 2007, vol. 35, No.3, Biochemical engineering journal ISSN 1369-703X; Abstract—2Pages.

V Kapur, J C Charkoudian, S B Kessler and JL Anderson; "Hydrodynamic permeability of hydrogels stabilized within porous membranes"; 1996, vol. 35, No. 9; Abstract—2Pages.

* cited by examiner

*Primary Examiner* — Ernest G Therkorn
(74) *Attorney, Agent, or Firm* — Eileen B. Gallagher

(57) ABSTRACT

The invention relates to a device for separating unwanted compounds from an antibody containing biological sample. The device comprises a porous support and a polymeric resin disposed within the pores of the porous support. The device may further comprise a viral clearance membrane upstream or downstream from the polymeric resin. Methods of use are also provided.

17 Claims, 2 Drawing Sheets

MEMBRANES AND ASSOCIATED METHODS FOR PURIFICATION OF ANTIBODIES

BACKGROUND

Purification of therapeutic or diagnostic biological molecules or entities, such as antibody, plasmid DNA, vaccines, or plasma fractions from endogenous impurities (host cell DNA or proteins) or adventitious contamination (endotoxin, virus or bacterium) is a growing field in bioseparation and bioprocessing. Large amounts of pure antibodies may often be necessary for immunological and therapeutical applications. In the last few years, monoclonal or recombinant antibodies and their constructs have become the largest class of molecules that are being investigated in clinical trials for therapeutics and diagnostics. Complementary to expression systems and production strategies, efficient purification protocols are required to obtain highly pure antibodies in a simple and cost-efficient manner. There is a need for developing less expensive, more scalable and faster purification techniques.

Traditional methods for purification, such as salt-based protein fractionation, or ultracentrifugation are not economical and are time consuming Bead-based chromatographic techniques, each relying on specific molecular interactions have been used for purification of antibodies and viruses as well and include affinity, hydrophobic interaction and ion-exchange chromatography. Chromatography, primarily on beads, has been used for purifying antibodies or viruses. Commonly used chromatographic techniques are based on the principle of interactions, including affinity chromatography, hydrophobic interaction chromatography, or ion-exchange chromatography. Efforts have been made in the past to design optimal stationary phases for each specific separation purpose. Such a stationary phase often comprises a support or base matrix attached to a ligand comprising binding groups. A combination of various chromatographic techniques may be used to develop a multimodal chromatographic separation technique for purification of biological macromolecules with higher purity and yield, in a cost-effective and efficient manner.

Alternatively, membrane chromatography has been used to achieve high efficiency and high-flux separations of biological molecules. However, to optimize a process related to the purification of a specific target molecule, a unique operating condition is often required. Moreover, the best separation matrix may vary for different samples, such as, antibody, endotoxin, or virus. For example, in the biotech industry, specific processes need to be designed for the purification of peptides and proteins (e.g., antibody); nucleic acids; or viruses. Moreover, for purification of antibodies, the type of antibody may be significant for the choice of separation matrix. Thus, alternative separation matrices are in need to provide a broad spectrum of choices for purification of the many new products that are constantly being developed.

Trace impurities may affect the capacity of membranes. Various membranes and chromatography resins have conventionally been used to remove trace impurities, such as DNA, host cell proteins, or protein aggregates. Proteins, sometimes form aggregates during freezing, and thawing procedures or process hold steps in downstream purification. Therefore, there is a constant need for removal of aggregated protein and trace impurities before proceeding to the viral clearance step and final formulation of the target protein molecule.

BRIEF DESCRIPTION

The invention generally relate to a novel separation device comprising a porous support; and a polymeric resin disposed within the pores of the porous support and methods for using the device for antibody purification. The purification process may be made more efficient by combining the polishing step with a virus removal step in the same unit operation. This can be accomplished by juxtaposing a separation matrix comprising the porous support and the polymeric resin with a virus clearance membrane in the same device.

In one embodiment, the invention provides a device for separating one or more unwanted compounds from an antibody containing biological sample. The said device comprising a porous support; and a polymeric resin disposed within the pores of the porous support wherein the polymeric resin comprises structural units derived from a vinyl cross linker; and an aromatic monomer comprising a quaternary ammonium group and at least two ring structures.

In one embodiment, the invention provides a device for separating unwanted compounds from an antibody containing biological sample. The device comprises a porous support; and a polymeric resin disposed within the pores of the porous support wherein the polymeric resin comprises structural units derived from a vinyl cross linker; and a monomer having structural unit derived from Formula I, Formula II, Formula III, or a combination thereof;

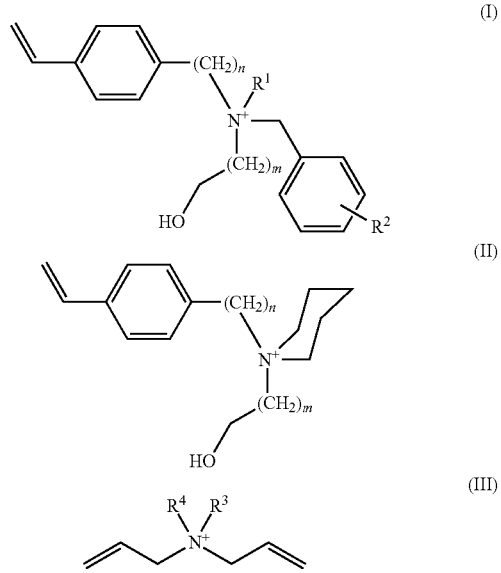

wherein R1 and R2 are independently a hydrogen, a C1-C20 alkyl, a C1-C20 substituted alkyl, an aryl, a substituted aryl, or a combination thereof, and m and n are independently integers between 1 and 5; R3 and R4 are independently a hydrogen, a C1-C20 alkyl, a C1-C20 substituted alkyl, a benzyl or a substituted benzyl. Furthermore, the polymeric resin is capable of selectively retaining one or more compounds present in the biological solution through a multimodal interaction.

In one embodiment, the device further comprises a viral clearance membrane capable of removing virus and a porous support containing the polymeric resin is positioned upstream or downstream of the viral clearance membrane.

In one embodiment, a method of separating antibodies from unwanted compounds present in an antibody containing biological sample, comprising adding the biological sample to the afore mentioned device such that said sample contacts the polymeric resin, selectively retaining one or more compounds present in the biological sample through a multimodal interaction; and collecting a flow-through effluent comprising unbound antibodies.

In another embodiment the method further includes the improved capacity of a viral clearance membrane with a biological sample through the use of a polishing step that incorporates the porous support containing the polymeric resin upstream of the viral clearance membrane within the same device.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
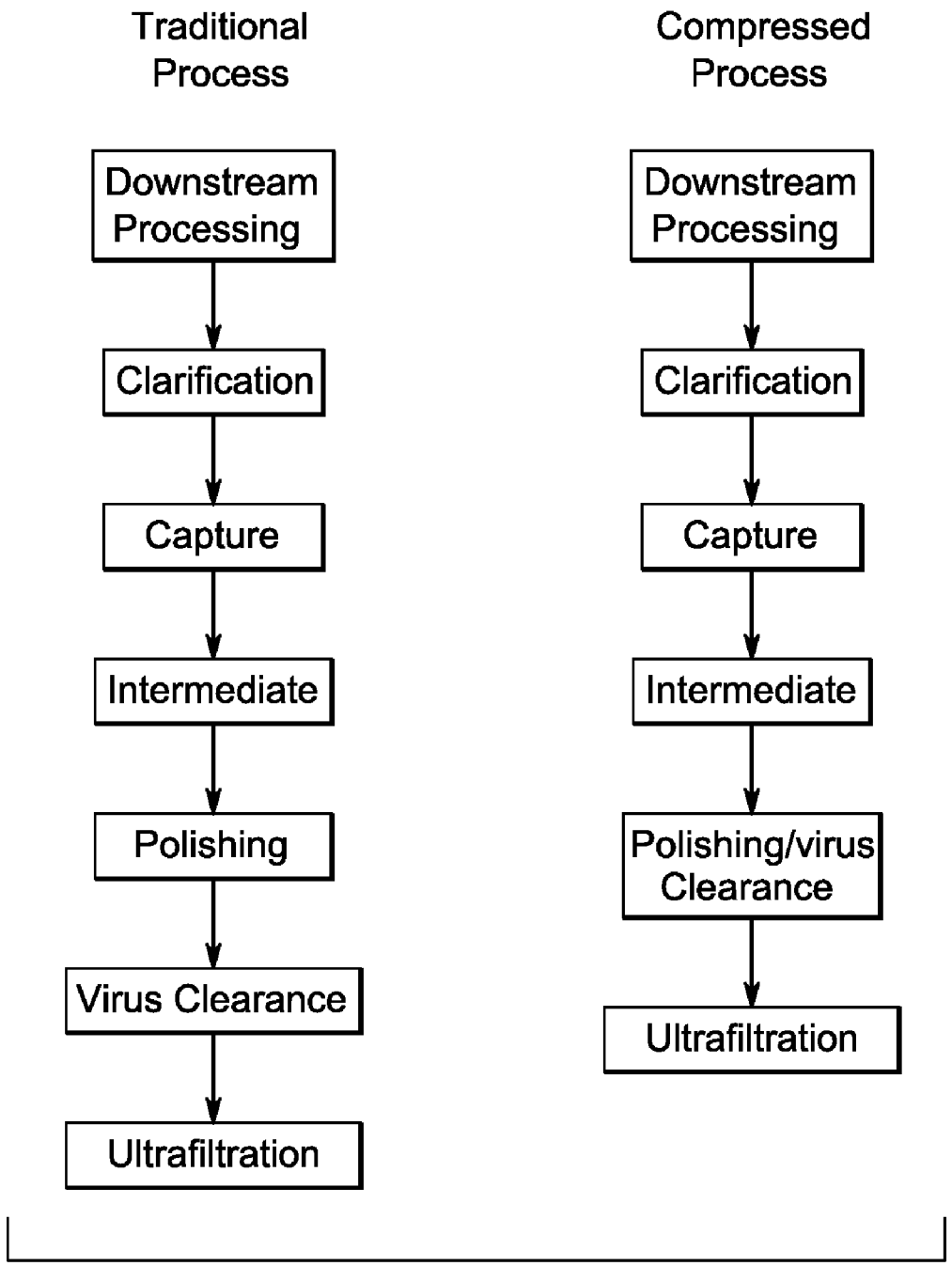
FIG. 1 shows two flowcharts illustrating a comparison between a traditional bioprocess and a compressed bioprocess for antibody purification.

To more clearly and concisely describe the subject matter of the claimed invention, the following definitions are provided for specific terms, which are used in the following description and the appended claims. Throughout the specification, exemplification of specific terms should be considered as non-limiting examples.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Definitions

The terms "antibody" and "immunoglobulin" are used interchangeably in the specification.

The term "Separation matrix" or "resin" refers to a material comprised of a support wherein the support has ligands directly or indirectly attached to it or is coated with crosslinked polymer and one or more ligands comprising functional groups have been coupled to the polymer. More specifically, separation matrix as used herein refers to a porous support having a polymer resin disposed within the pores of the porous support.

The term "Multi-modal separation matrix" or "mixed mode separation matrix" refers to a separation matrix capable of providing at least two different, but co-operative sites that interact with one or more compounds for binding. For example, one of these sites may provide a charge-charge interaction between the ligand and the compound of interest.

The other site(s) may provide electron acceptor-donor interaction and/or hydrophobic and/or hydrophilic interaction. Electron donor-acceptor interactions include, but are not limited to, hydrogen-bonding interactions, $\pi$-$\pi$ interactions, cation-$\pi$ interactions, charge transfer interactions, dipole-dipole interactions, or induced dipolar interactions.

The term "Aliphatic radical" refers to an organic radical having a valence of at least one, consisting of a linear or branched array of atoms that is not cyclic. Aliphatic radicals comprise at least one carbon atom. The array of atoms comprising the aliphatic radical may include heteroatoms such as nitrogen, sulfur, silicon, selenium or oxygen, or may be composed exclusively of carbon and hydrogen. Aliphatic radical encompasses, as part of the linear or branched array of atoms which is not cyclic, a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, 4-methylpent-1-yl radical is a C6 aliphatic radical comprising a methyl group, the methyl group being a functional group which is an alkyl group. Similarly, the 4-nitrobut-1-yl group is a C4 aliphatic radical comprising a nitro group, the nitro group being a functional group. An aliphatic radical may be a haloalkyl group which comprises one or more halogen atoms that may be the same or different. Halogen atoms may include, for example; fluorine, chlorine, bromine, or iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si-), t-butyldimethylsilyl, 3-trimethyoxysilylpropyl (i.e., (CH$_3$O) 3SiCH$_2$CH$_2$CH$_2$—), vinyl, vinylidene, and the like. By way of further example, a C1-C10 aliphatic radical contains at least one but no more than 10 carbon atoms. A methyl group (i.e., CH$_3$—) is an example of a C1 aliphatic radical. A decyl group (i.e., CH$_3$ (CH$_2$)$_9$—) is another example of a C10 aliphatic radical.

The term "surface" means all external surfaces, and includes in the case of a porous support outer surfaces as well as inner surface of the pores.

The term "flow-through" refers to a liquid coming out from the separation matrix after loading the mobile phase to the separation matrix. The flow-through may comprise proteins or other compounds that did not bind to the separation matrix.

The term "eluent" refers to a solution or a buffer of suitable pH and/or ionic strength that is used to release one or more compounds from a separation matrix.

The term "unwanted compound" refers to a substance that can be bound to the chromatography ligand or to the separation matrix. The unwanted compound may be biomolecules such as proteins (which may exclude target compounds like an antibody), leached protein-A, DNA, viruses, endotoxins, nutrients, and components of a cell culture medium, antifoam agents, and antibiotics. Unwanted compounds may also refer to other products that may typically be termed "impurities"

for example aggregates, host cell proteins, DNA, viruses, endotoxin, misfolded species (e.g., misfolded proteins), or denatured species.

The term "capture step" refers in the context of liquid chromatography to the initial step of a separation procedure. Most commonly, a capture step includes a degree of clarification, where as concentration, stabilization and a significant purification from soluble impurities are more commonly ascribed to this step. After the capture step, an intermediate purification may follow, which further reduces remaining amounts of impurities such as host cell proteins, DNA, viruses, endotoxins, nutrients, components of a cell culture medium, antifoam agents antibiotics, or product-related impurities such as aggregates, misfolded species and aggregates. Lastly, a series of polishing steps may be taken to remove trace impurities such as the remaining host cell proteins, DNA, viruses, protein aggregates and endotoxins.

The term "polishing step" refers in the context of liquid chromatography following the initial purification step of a separation procedure. Most commonly, a polishing step is employed to reduce trace impurities such as host cell proteins, DNA, viruses, endotoxins and protein aggregates; these impurities are more commonly ascribed to this step. Polishing steps can be performed in a flow through mode of operation, where the target molecule is not bound by the separation matrix and trace impurities are bound. Viral clearance via filtration most commonly follows a polishing step as a separate unit operation.

The term "disposable" means herein in the context of chromatography chambers and separation matrices in a device, a matrix that is intended for single use, or a limited number of uses. Disposable devices (e.g., column, beads or separation matrices, or porous supports) are advantageously used to remove contaminants that are harmful even in very small amounts. Disposable devices are desirable for sterile processing of the biomolecules so as to reduce the likelihood of introducing contaminants and cross contamination.

One or more embodiments comprise a device for separating unwanted compounds from an antibody containing biological sample comprising a porous support; and a polymeric resin disposed within the pores of the porous support. The device itself may be in the form of a chromatographic chamber, a tubular column, monoliths; filters or membranes; capillaries; microfluidic chips, a pleated cartridge or capsule or a cassette, a spiral, a hollow fiber, syringe filter, manifold, or a multi-well plate. All of the devices comprise a porous support coated with the polymeric resin of the invention.

In some embodiments, a polymeric resin is disposed within the pores of a porous support structure. The porous support may be made in the form of a membrane, a web, a filter, a fiber, or a mesh.

The porous support comprises a plurality of pores. The diameter of the pores may range from about 0.1 microns to about 10 microns. In some specific embodiments, the diameter of the pores ranges from about 2 microns to about 5 microns. The pores may be of identical sizes/shapes or of different sizes/shapes. The pores may be circular, elliptical, rectangular, square, or triangular in shape.

The porous support may be made using an organic or inorganic material. In some embodiments, the porous support is made using a polymer. The porous support may be prepared using a natural polymer (e.g. agarose, agar, cellulose, dextran, chitosan, konjac, carrageenan, gellan, alginate, pectin, or starch) or from a synthetic polymer (e.g. Polyarylether, such as polyphenylene ether, polyethersulfone, polyetherketone, polyetherimide, polyphenylene, polyvinyl polymers such as polystyrene, polyacrylates or polymethacrylates, polyvinyl esters, polyacrylamides, polyvinylesters, polyvinylamides, polyvinylidene difluoride (PVDF), polytetrafluoroethylene (PTFE), polycarbonates, polyesters. The polymer used may be a homopolymer, a copolymer, a cross-linked polymer, a block copolymer a random polymer or a polymer blend. Often blends of the aforementioned polymers with water soluble polymers may be processed by thin-film coagulation, the water soluble polymer acting to control pore morphology. Suitable polymers that may be used for making the porous support include, but are not limited to, polysulfones, polyethersulfones, expanded polytetrafluoroethylene (e-PTFE), polyvinylidenefluoride (PVDF), polyphenyleneoxides, polycarbonates, polyesters, cellulose, or cellulose derivatives. In some other embodiments, the support is prepared from an inorganic polymer, such as silica.

In some embodiments, the polymeric resin disposed within the pores of the porous support comprises structural units derived from a vinyl cross linker; and an monomer having structural units derived from Formula I, Formula II, Formula III or a combination thereof.

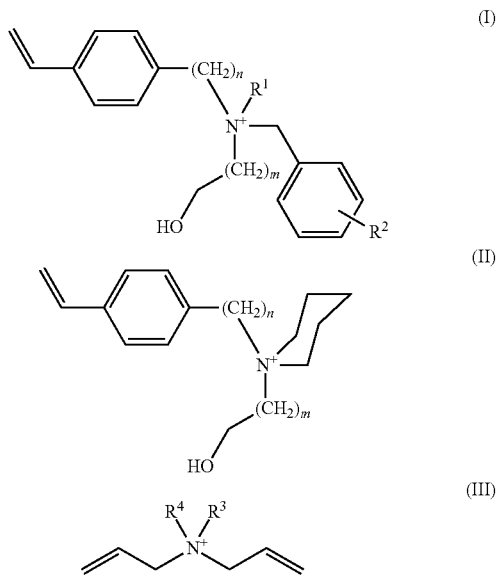

In Formula I, $R^1$ and $R^2$ are independently hydrogen, a $C_1$-$C_{20}$ alkyl, a $C_1$-$C_{20}$ substituted alkyl, an aryl, a substituted aryl, or a combination thereof. In Formula I and II, m and n are independently integers between 1 and 5. In some embodiments, the monomer is comprised of at least two ring structures.

As shown in Formula (I), the styrene-substituted quaternary amine comprises a $R^1$ group, which is connecting to the nitrogen of the amine, while $R^2$ is a substituted group that may attach to the ortho, meta, or para position of the benzene ring. While $R^1$ is hydrogen, Formula (I) represents a tertiary amine. $R^1$ may comprise 1-20 carbon atoms containing alkyl, such as 2-16 or 3-18 carbon atoms containing alkyl with or without substitution. The substituted group $R^2$ comprises 1-20 carbon atoms. $R^2$ may comprise 1-20 carbon atoms, such as 2-18 carbon atoms, which are optionally substituted. While $R^2$ is hydrogen, the benzene ring is attached to nitrogen via a $CH_2$-group.

In some embodiments, $R^1$ may be an aryl or a substituted aryl. The aryl ring system of $R^1$ may comprise one or more substituted or non-substituted phenyl groups, provided the substitution(s) do not impair the binding properties of the.

Thus, $R^1$ may comprise one or more aromatic rings, for instance a phenylene, a biphenylene or a naphthalene structure and other aromatic ring systems. Aromatic rings may be heterocyclic, contain one or more nitrogen, oxygen or sulphur atoms, for instance a pyridine, pyrimidine, pyrrole, imidazole, thiophene, or pyran. Illustrative substituted $R^1$ groups are selected from the group consisting of hydroxyphenyl (2-, 3- and 4-); 2-benzimadozolyl; methylthioxyphenyl (2-, 3- and 4-); 3-indolyl; 2-hydroxy-5-nitrophenyl; aminophenyl (2-, 3- and 4-); 4-(2-aminoethyl)phenyl; 3,4-dihydroxyphenyl; 4-nitrophenyl; 3-trifluoromethylphenyl; 4-imidazolyl; 4-aminopyridine; 6-aminopyrimidyl; 2-thienyl; 2,4,5-triaminophenyl; 4-aminotriazinyl; and 4-sulphoneamidophenyl. In a specific embodiment, $R^1$ is a non-substituted phenyl. In an alternative embodiment, $R^1$ is a phenyl substituted with one or more OH groups.

Further, $R^1$ or $R^2$ may be substituted with any suitable substituent, as long as the binding properties of the ligand are not impaired. For example, if a more hydrophilic ligand is desired, it may comprise one or more hydrophilic groups, such as OH groups. Alternatively, substitution may increase the hydrophobicity of the ligand, in which case the ligand may comprise one or more hydrophobic groups, such as an alkyl group and/or a fluorine-containing group. Finally, substitution may be used to introduce one or more additional functionalities, such as charged entities to increase the multi-modal character of the ligand. Further, the $R^1$ and $R^2$ may be linear or branched, as long as the branches do not impair the binding properties of the ligand.

As shown in Formula II, a piperidine ring is attached to $CH_2$ linked to the substituted benzene, more specifically, vinyl benzene. The piperidine ring is present as a pendant hydrocarbon chain attached to the vinyl benzene. The m and n are independently integers between 1 and 5. In some embodiments, the ligand that binds to one or more compounds present in the biological sample comprises vinyl benzene or styrene.

In Formula (III), $R^3$ and $R^4$ are independently at each occurrence a hydrogen, a C1-C20 alkyl, a C1-C20 substituted alkyl, or a combination thereof. In certain embodiment, Formula III comprises two vinyl groups attached to the nitrogen atom and $R^3$ and $R^4$ are independently at each occurrence, hydrogen atoms. In another $R^3$ or $R^4$ may comprise 2-18 carbon atoms, which are optionally substituted. In still another Formula III comprises at least two ring structures.

In another embodiment, $R^3$ and $R^4$ are independently at each occurrence an aryl, or a substituted aryl groups. The aryl ring system $R^3$ or $R^4$ may comprise one or more substituted or non-substituted phenyl groups, provided the substitution(s) do not impair the binding properties of the ligand. Thus, $R^3$ or $R^4$ may comprise one or more aromatic rings, for instance a benzyl, phenylene, a biphenylene or a naphthylene structure and other aromatic ring systems (adhere moiety). Aromatic rings may be heterocyclic, i.e. contain one or more heteroatoms (e.g., nitrogen, oxygen or sulphur atoms), for instance a pyridine, pyrimidine, pyrrole, imidazole, thiophene, or pyran. Illustrative substituted $R^3$ and $R^4$ groups are selected from the group consisting of hydroxyphenyl (2-, 3- and 4-); 2-benzimadozolyl; methylthioxyphenyl (2-, 3- and 4-); 3-indolyl; 2-hydroxy-5-nitrophenyl; aminophenyl (2-, 3- and 4-); 4-(2-aminoethyl)phenyl; 3,4-dihydroxyphenyl; 4-nitrophenyl; 3-trifluoromethylphenyl; 4-imidazolyl; 4-aminopyridine; 6-aminopyrimidyl; 2-thienyl; 2,4,5-triaminophenyl; 4-aminotriazinyl; and 4-sulphoneamidophenyl. In an advantageous embodiment, $R^3$ or $R^4$ is a non-substituted phenyl. In an alternative embodiment, $R^3$ or $R^4$ is a phenyl substituted with one or more OH groups.

In some embodiments, $R^3$ comprises structural units derived from Formula IV. $R^5$ and $R^6$ are independently hydrogen, a $C_1$-$C_{20}$ alkyl, a $C_1$-$C_{20}$ substituted alkyl, an aryl, a substituted aryl, or a combination thereof, and m and n are independently integers between 1 and 5.

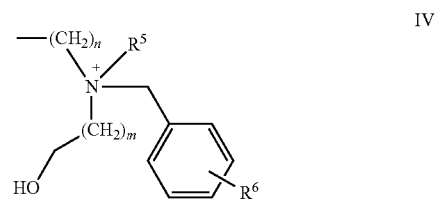

IV

In certain embodiments, the polymeric resin may further comprise structural units derived from Formula V

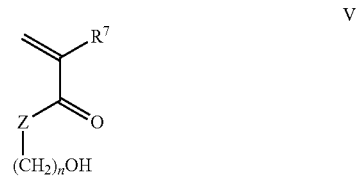

V wherein Z is NH or O, $R^7$ is hydrogen or methyl, a $C_1$-$C_5$ alkyl, a substituted alkyl, or a combination thereof, and n is an integer between 1 and 5.

As shown in the Formula I, II, and III, the ligand according to the invention comprises a vinyl substituted benzene derivative, which is suitable for cross-linking and adhering to a porous support, thus creating a coupled ligand which comprises a quaternary amine and a phenyl group. Consequently, as immobilized, the ligand may function as a multi-modal anion exchange ligand, since in addition to the positively charged quaternary amine group it also comprises the aromatic ring structure, which is hydrophobic.

Thus, the polymeric resin commonly comprises a plurality of ligands. In a specific embodiment, the polymer matrix may comprise a first ligand derived from Formula I, II, or III, as described above in combination with a second kind of ligand or a mixture of ligands. The second ligand may also be selected from Formula I, II, or III. The first ligand may be present in at least about 30%, preferably at least about 50%, more preferably at least about 70% and most preferably at least about 90% of the total ligand amount. Such a combined ligand separation device may be designed to increase interactions with one or more unwanted compounds to improve the separation properties. The second kind of ligand may comprise one or more charged groups such as a cation exchanger which is used to elute target compounds by charge repulsion; hydrophobic groups; groups capable of hydrogen-bonding; affinity groups or the like.

In some embodiments, the polymeric resin comprises cross linkers, wherein the cross linkers may be vinyl cross linkers. The vinyl cross linkers comprise N',N"-methylenebisacrylamide. The vinyl cross linker is capable of being activated through a treatment of heat, light, radiation, or a combination thereof. In some other embodiments, the cross linker may be a non-vinyl cross linker.

The separation device comprises a porous support and a polymeric resin disposed within the pores of the porous support. As used herein the combination of the porous support and the polymeric resin may be referred to interchangeably as a separation matrix or a polishing matrix as it relates to its mode of action; separation step and/or polishing step.

Separation matrices of the device comprises a polyethersulfone porous support and a polymeric resin comprising structural units derived from one or more of monomer 1, monomer 2, and cross linker as shown in Table 1. For prototype 1, monomer 1 is derived partially from Formula IV, where $R^5$ is methyl group, n is 1 and one H is attached to C of $CH_2$ and $(CH_2)_m$—$CH_2$—OH part is replaced by another methyl group which is now attached to N. Prototype I may further comprise structural unit (structure 2) derived from Formula III as shown in Table 1. For prototype 2, structural unit (monomer 1) is derived from Formula II. Prototype 3 and prototype 4 comprise structural units (monomer 1) derived from Formula I. Prototype 4 further comprises structural unit (monomer 2) derived from Formula V. N',N''-methylenebisacrylamide was used as a vinyl cross-linker for each prototype. Water and methanol were used as solvent for prototype 2, 3, and 4. Only water was used as a solvent for prototype 1 (as shown in Table 1). For all the prototypes, Irgacure 2959 was used as an initiator and E-beam was used for curing the polymer. The "membrane prototype" has interchangeably used as a "separation matrix".

TABLE 1

Membrane Prototype Compositions.

| Prototype | Monomer 1 | Monomer 2 | cross-linker | Initiator | Solven | Cure Method |
|---|---|---|---|---|---|---|
| Prototype 1 | [structure with vinyl phenyl $CH_2$-$NMe_3^+$ $Cl^-$] | [allyl-diallyl ammonium $Cl^-$] | [N,N'-methylenebisacrylamide] | Irgacure 2959 | Water | E-beam |
| Prototype 2 | [vinyl benzyl piperidinium with hydroxyethyl, $Cl^-$] | None | [N,N'-methylenebisacrylamide] | Irgacure 2959 | Water/ MeOH | E-beam |
| Prototype 3 | [vinyl benzyl N-methyl-N-(hydroxyethylphenyl) ammonium $Cl^-$] | None | [N,N'-methylenebisacrylamide] | Irgacure 2959 | Water/ MeOH | E-beam |

TABLE 1-continued

Membrane Prototype Compositions.

| Prototype | Monomer 1 | Monomer 2 | cross-linker | Initiator | Solvent | Cure Method |
|---|---|---|---|---|---|---|
| Prototype 4 | (styrene with benzyl-methyl-(2-hydroxyethyl)ammonium chloride substituent) | N-(hydroxymethyl)acrylamide | N,N'-methylenebisacrylamide | Irgacure 2959 | Water/MeOH | E-beam |

The device according to the invention may take any other shape conventionally used in separation, such as a chromatographic chamber, monoliths; filters or membranes; capillaries; microfluidic chips, a tubular column, a pleated cartridge or capsule a cassette, a spiral, a hollow fiber, a syringe filter, or a manifold. For example, the device may comprise a membranous structure, such as a single membrane layer, or multiple layers of membranes that compose a filter device.

In one embodiment the separation matrix may be dried prior to or after use. The dried structure may be soaked in liquid to regenerate its original form before use.

The polymeric resin is capable of retaining one or more unwanted compounds present in a sample. In one embodiment, the one or more unwanted compounds may be retained on the membrane by binding of one or more unwanted compounds to the membrane. The polymeric resin is capable of binding one or more unwanted compounds present in a sample. The sample may comprise one or more target compounds like antibodies and one or more unwanted compounds like host cell proteins, DNA, viruses, endotoxins etc. In one embodiment, the polymeric resin is capable of retaining one or more unwanted compounds present in a sample through binding. The unwanted compounds may bind to the polymeric resin by a multi-modal interaction. The multi-modal interaction, for non-limiting example, may be ionic interaction, electrostatic interaction, hydrophobic interaction, Van der Waals interaction, hydrogen bonding interaction or dipole-dipole interaction. The multi-modal interaction may comprise at least two of hydrogen bonding interactions, hydrophobic interaction or ionic interaction. In one embodiment, the multi-modal interaction may include hydrogen bonding interaction, and hydrophobic interaction. In another embodiment, the multi-modal interaction may include hydrogen bonding interaction and ionic interaction. In yet another embodiment, the multi-modal interaction may include hydrophobic interaction and ionic interaction.

In some embodiments, the sample is a biological sample containing antibodies, and may comprise one or more compounds apart from the molecules of interest. The "molecule of interest" or "target compounds" as referred herein is a molecule that needs to be separated from a mixture containing unwanted compounds along with the molecule of interest. For example, the molecule of interest may be an antibody that needs to be separated from a mixture containing the antibody and host cell proteins. The molecule of interest (target compounds) may include but not limited to proteins, peptides, amino acids, nucleic acids (e.g. DNA, RNA), endotoxins, viruses, and antibodies. In some embodiments, the unwanted compounds may be DNA, endotoxins, viruses, protein aggregates, or host cell proteins. The ligands of the polymeric resin may be selected in such a way that the molecules of interest present in the sample do not bind to the polymeric resin, and are passed through the matrix. The molecule of interest may then be processed further in subsequent downstream operations from the flow-through. The one or more unwanted compounds present in the biological sample may bind to the polymeric resin. The polymeric resin may interact with the one or more unwanted compounds present in sample through specific binding sites or via electrostatic interactions employing the charged sites (e.g., a negative charge) present on the one or more compounds. It is possible that some unwanted compounds may not bind to the resin, and are passed through the matrix in flow-through stream. Hence further purification may be necessary to remove these unwanted compounds from the molecule of interest. This may be achieved by a separate structure having a different polymeric resin comprising a different ligand moiety to further improve the polishing step. The unwanted compounds that bound to the polymeric resin may comprise one or more hydrophobic sites. The unwanted compounds may comprise anionic charged groups that may interact with the positively charged groups present in polymeric resin.

For small-scale purification, any of the referenced device formats in small area configurations may be used to improve purity as a polishing unit operation. For the step of polishing by removing impurities (or unwanted compounds) from a therapeutic or diagnostic biologic molecule, such as antibody, small tubular column or syringe filters may be useful. One or more inlet and outlet may be attached to the membrane device to maintain inward and outward flow of the mobile phase. In one embodiment, the device may be in the form of a single layer or multi-layer format of the separation matrix. The device may be connected to a pump or a pressure vessel attached to the inlet of the device to maintain a flow rate through the separation matrix. In a specific embodiment, the device may be a single layer or a multi-layer format of the separation matrix and may be sterilized prior to use.

The device, in some embodiments, may further comprise an additional separation membrane. The additional membrane may be capable of polishing the target molecule in a flow through mode of operation, by selectively removing certain compounds from the biological sample. This additional polishing step may be positioned after an intermediate purification operation as shown in the traditional process in FIG. 1. In some embodiments, the additional polishing step has a capacity of removing trace impurities such as host cell proteins, DNA, endotoxin, viruses and/or aggregated antibodies. FIG. 1 shows the process compression that incorporates the embodiment of a combined polishing step with a dedicated viral clearance step.

Figure 2:
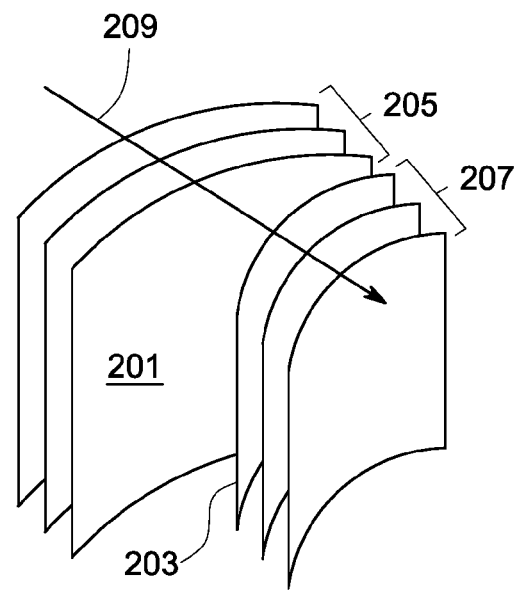
FIG. 2 shows a configuration illustrating the position of the polishing membrane and position of the of the viral clearance membrane relative to the direction of flow in the device.

In certain embodiments, the device may comprise a viral clearance membrane, which is positioned adjacent to the separation matrix. This is illustrated in FIG. 2 showing a separation matrix which functions as a polishing membrane 201 and the virus clearance membrane 203. In some embodiments, a series of separation matrices (for polishing) and virus clearance membranes may be present in the device.

The FIG. 2 further illustrates the position of the membranes relative to the direction of flow 209 in the device. Multiple layers of a separation matrix 205 are in contact with multiple layers of a virus clearance membrane 207. An interface between the last polishing membrane 201 of the layer and the first virus clearance membrane 203 of the layer constitutes a demarcation of a polishing step and a viral clearance step within the device.

In one embodiment, the device comprises both separation matrices for polishing the impurites and viral clearance membranes to remove viruses, wherein the separation matrices are juxtaposed with the viral clearance membranes. In one embodiment, the separation matrix (or matrices) may be juxtaposed upstream to the virus clearance membrane. In another embodiment, the separation matrix (matrices) may be juxtaposed downstream to the virus clearance membrane.

In a specific embodiment, the separation device may be attached to a display device wherein details of the flow rate, time, purity or salt concentration can be determined The separation device, more specifically the porous support containing the polymeric resin may be a part of a separation system comprising one or more of a porous support containing the polymeric resin, a controller, a computer, a display device, a liquid (mobile phase) handling system, a flow-through collection system. The separation system may be automated to perform one or more of its function with or without an operator intervention.

In some embodiments, the separation device may be provided in a sterile condition and may be disposed of after single use. The single use membrane device may be described as a disposable membrane device. An advantage of using disposable membrane devices for purification of therapeutic compounds such as antibodies is that it enables avoiding cross-contamination between two different processes. The membrane device may be in the form of a disposable monolith, a disposable tubular column, a disposable pleated cartridge, a disposable capsule, a disposable cassette, a disposable spiral filter, a disposable hollow fiber filter, a disposable syringe filter, or a disposable manifold.

In some embodiments, the separation device may be re-usable. In case of a re-usable device, the matrix is washed several times with eluent after passing the mobile phase through the matrix. The flow through of the final eluent may be tested to make sure that there are no proteins or peptides or other compounds present in the eluent. The matrix may then be equilibrated using a suitable buffer for further use.

In some embodiments, the device is further sterilized by suitable methods prior to use. Sterilization may be carried out by heat treatment such as autoclaving or exposing the internal matrix to saturated steam); by radiation in sufficient dose up to and including 45 kGry; or by using any other conventional methods for sterilization.

In one embodiments, a method of preparing a device for separating unwanted compounds from an antibody containing biological sample is provided wherein the method comprises the steps of providing the separation matrix juxtaposed to a viral clearance membrane in a device; and equilibrating the device with suitable buffer. In some embodiments, the separation matrix of the invention may be used for protein purification. The protein may be an antibody; an antibody fragment; or a fusion protein comprising an antibody. In another embodiment, the separation matrix may be used for the separation of any other compound, e.g. one selected from the group consisting of polypeptides, oligonucleotides, nucleic acids (e.g. DNA, RNA), plasmids; virus; prions, cells (e.g., prokaryotic or eukaryotic cells), lipids, carbohydrates, organic molecules, drug targets; or diagnostic marker molecules. As the skilled person in this field may realize, in the present application, the term separation is used for purification; isolation; and removal of unwanted compounds, but it also encompasses identification of a target compound such as antibody for diagnostic purposes.

In one embodiment, a method of separating antibodies from other unwanted compounds present in a sample is provided comprising adding a sample to a device whereby the device comprises a separation matrix and a virus clearance membrane. The sample is contacted with the separation matrix and passed through the separation matrix, followed by contacting with the virus clearance membrane and finally passing through the virus clearance membrane. In an alternative embodiment, the contacting and passing of the samples through the virus clearance membrane may precede the separation matrix. Unbound antibodies may be collected from the device in a flow-through mode of operation. The sample may be passed through device in the embodiments described above using the assistance of a gravitational field, pump, pressure vessel, or a combination thereof.

The sample that is passed through the device may be a supernatant obtained from a cell extract. In some embodiments, prior to contacting the sample with the separation matrix, one or more pre-purification steps may be performed. The one or more of pre-purification steps may include mechanical filtration, centrifugation, ultracentrifugation, gel filtration, ion exchange chromatography, affinity chromatography, or electrophoresis.

The compound of interest (target compounds) such as an antibody may be separated from one or more other unwanted compounds of a biological sample by contacting a mobile phase comprising said biological sample with the separation matrix as described above. In a specific embodiment, the present method may be carried out using the principles of liquid chromatography, i.e. by passing a mobile phase over device comprising the separation matrix according to the invention. In an alternative embodiment, the present method may be carried out using the principles of liquid chromatography, i.e. by passing a mobile phase over the device comprising the polishing membrane and a viral clearance membrane according to the invention.

In one embodiment of the present method, unwanted compounds are adsorbed to the separation matrix while the desired compound, such as the antibodies, remain in the mobile phase without being adsorbed. In another embodiment, the unwanted compounds such as aggregated or misfolded proteins or peptides, or viruses are adsorbed to the viral clearance membrane while the desired compound, such as the antibodies, remain in the mobile phase without being adsorbed. As understood by the skilled person in this field, the nature and identity of the adsorbed compounds will depend on the origin of the biological sample. Non-limiting examples of unwanted compounds adsorbed in the matrix (where desired antibodies are not adsorbed) are cells and cell debris; proteins (except desired antibodies) and peptides; aggregated form of proteins or peptides, nucleic acids, such as DNA and RNA, endotoxins, viruses, residues from the culture media etc. In a specific embodiment, the separation matrix of the present invention or the viral clearance membrane or both are provided in a membrane device and the mobile phase is passed through said device by gravity and/or pumping or pressure, the antibodies being recovered in the flow-through. In a specific embodiment, the membrane device may be a chromatographic device.

In one embodiment, the present method constitutes a polishing step using a flow through mode of operation. In a specific embodiment, the biological sample is a crude feed, which is filtered before contacting with the polishing membrane (separation matrix) and viral clearance membrane according to the invention. Consequently, this embodiment would constitute a polishing step even though the biological sample has been pre-purified by mechanical means. The host cells that produce antibodies may also comprise a number of other proteins commonly known as host cell proteins. Such host cell proteins may include enzymes (e.g. proteases), and other proteins produced by the host cells. Thus, in one embodiment, the host cell proteins of the biological sample are substantially removed by the present method, by adsorbing the host cell proteins to the separation matrix.

In alternative embodiments, the present method may be used as a second, third or even fourth chromatography steps in a cleaning protocol, such as an intermediate purification or polishing step. Thus, in one embodiment, the mobile phase comprises an antibody-containing biological sample applied to the present separation matrix.

The present method is useful to separate any monoclonal or polyclonal antibody, such as antibodies originating from mammalian hosts, e.g. mice, rodents, primates and humans, or antibodies originating from hybridomas. In one embodiment, the separated antibodies are collected from human or humanized antibodies. The antibodies may be of any class, i.e. selected from the group that consists of IgA, IgD, IgE, IgG, or IgM. In one embodiment, the antibodies are capable of binding to Protein A, or Fc-containing antibody fragments or fusion proteins. In a specific embodiment, the antibodies are immunoglobulin G (IgG), such as IgG1. In one embodiment, the present method is used to purify antibodies having an isoelectronic point (pI) in the range of 6-9, specifically in the range of 7-8. In a specific embodiment, the pI of the purified antibodies is about 9. In the present context, it is to be understood that the term "antibodies" also includes antibody fragments and any fusion protein that comprises an antibody or an antibody fragment. Thus, the present invention also encompasses the separation of fragments of any one of the above-mentioned antibodies as well as fusion proteins comprising such antibodies. In one embodiment, the antibodies are monoclonal antibodies. In a specific embodiment, the antibodies are humanized antibodies.

The present method may not require any elution of the antibody product from the separation matrix within the device. Avoiding a specific elution step is attractive from a process point of view, since fewer steps will result in a more rapid purification protocol and consequently reduce the process cost. In addition, antibodies are sensitive to certain conditions that may impair their folding pattern; or degrade them by cleaving the peptide bonds. Thus, even though elution conditions for anion-exchangers in general do not involve any extreme chemicals, the change of salt and/or pH may affect a sensitive antibody, the effect varying from species to species depending on the pI, charge distribution etc. Further, in some embodiments, the present method avoids adding an eluent and applying eluting conditions to the desired compounds. To obtain the most suitable conditions for adsorption of compounds, the biological sample may combine with a suitable buffer or other liquid to provide a mobile phase.

It may also be possible to employ the present method under conditions conventional for anion-exchange chromatography, which commonly involves adsorption at a relatively low salt concentration. Thus, in one embodiment of the present method, the conductivity of the mobile phase is in the range of 1-25 mS/cm. In some embodiments, the conductivity of the mobile phase is in the range of 7-15 mS/cm. The pH of the mobile phase may be about 5-8. If it is desired to subsequently release the adsorbed compounds, for example for re-using the separation matrix, elution may be carried out at a higher salt concentration (e.g. by using an increasing salt gradient). The pH value may also or alternatively be shifted, e.g. be a decreasing pH gradient, to elute adsorbed compounds.

The method may be adapted to adsorb a specific compound, advantageously by control of the pH and/or conductivity. For example, in the separation of antibodies, different classes of antibodies have different charges and charge distribution patterns. The combination of charge distribution pattern and the purpose of the separation will decide whether antibodies are more preferable to adsorb or to let them pass through the device without being adsorbed.

The antibodies that need to be separated from unwanted other compounds may originate from any well known source, such as cells cultured at a surface, or from batch-wise or continuous cell culture in fermentation tanks or vessels. The sample containing the antibody may be a liquid, a suspension, or a semi-solid. In a specific embodiment, the sample is a liquid sample. The sample may comprise a crude cell extract or maybe a partially purified cell extract. The sample may be collected from a patient body. In one embodiment, the biological sample may be a supernatant obtained from cell fermentation.

EXPERIMENTALS

Example 1

Synthesis of Monomer Derived from Structural Units

Unless otherwise mentioned, chemicals were purchased from Aldrich, USA and used as received. Solvents were obtained from Fisher, USA.

Synthesis of Vinylbenzyl monomers: The general synthetic approach for making quaternary ammonium salt monomers derived from vinylbenzyl chloride is described herein. Vinylbenzyl chloride was reacted with a tertiary amine using dichloromethane or methanol as a solvent. Reaction time was ranged from 3-24 h at a room temperature or 3.5-6 h at 65° C. for tertiary amines comprising bulky groups (such as, piperidine ethanol and N-benzyl-N-methyl-ethanolamine). Reaction completion was determined by $^1$H NMR analysis for the reaction product. The final product was either used directly or isolated by solvent evaporation and was used without further purification. The reaction products were typically isolated in 95% yield with more than 95% purity as assessed by $^1$H NMR analysis.

Synthesis of 1-(2-hydroxyethyl)-1-(4-vinylbenzyl)piperidinium chloride or Vinylbenzyl[piperidine-ethanol]ammonium chloride: Vinylbenzyl chloride was filtered through basic alumina and was used immediately after filtration. To a 250 ml round bottom flask 24.83 g of vinylbenzyl chloride (162 mmol) and 50 ml dichloromethane (DCM) were added followed by addition of 20.99 g (162 mmol) of 2-piperidinethanol. The reaction mixture was stirred for 3.5 h at 65° C. The solvent was evaporated under vacuum and the product was used without further purification. The product was >95% pure as assessed by $^1$H-NMR.

Synthesis of N-benzyl-2-hydroxy-N-methyl-N-(4-vinylbenzyl)ethanamonium chloride or Vinylbenzyl[N-benzyl-N-hydroxyethyl-N-methyl]ammonium chloride: Vinylbenzyl chloride was filtered through basic alumina and was used immediately after filtration. In a 250 ml round bottom flask 34.0 g of vinylbenzyl chloride (220 mmol), and 60 ml of dichlromethane (DCM) were added followed by addition of 36.8 g (220 mmol) of N-benzyl-N-hydroxyethyl-N-methyl amine. The reaction mixture was stirred for 3.5 h at 65° C. The solvent was evaporated under vacuum and the product was used without further purification. The product was >95% pure as assessed by $^1$H-NMR.

Synthesis of N-benzyl-2-hydroxy-N-methyl-N-(4-vinylbenzyl)ethanamonium chloride or Vinylbenzyl[N-benzyl-N-hydroxyethyl-N-methyl]ammonium chloride: In a 1 L flask 101 g of vinylbenzyl chloride (661 mmol), and 109.3 g (661 mmol) of N-benzyl-N-hydroxyethyl-N-methyl amine were added followed by addition of 60 ml methanol. The reaction mixture was stirred for 5.5 h at 65° C. The reaction mixture was used without further purification. The product was >95% pure as assessed by $^1$H-NMR.

Synthesis of N-benzyl-N,N-Diallyl-N-methylammonium Chloride: A 500 mL one round bottom flask was charged with 36.2 g (0.288 mol) of benzylchloride, 16.0 g of diallylmethylamine (0.144 mol) and 140 g of acetonitrile. The solution was refluxed for 2 days. The solution was concentrated and product was precipitated in diethyl ether. The crude viscous oil was dissolved in water (40 mL) and washed thrice with diethyl ether (3×100 mL). The aqueous phase was collected, the solvent was evaporated and the resulting oil was dried in vacuum at 50° C. 30.0 g (88%) of a viscous oil yield after said process. 1H-NMR (400 MHz, CDCl3/CD3OD) shows peaks at 7.60-7.10 ppm (m, 5H); 6.05-5.75 ppm (m, 2H); 5.70-5.40 ppm (m, 4H); 4.76 ppm (s, 2H), 4.20-3.80 ppm (m, 4H); and 2.94 ppm (s, 3H).

Example 2

Membrane Fabrication and E-Beam Cure Method

Membrane fabrication material: Unless otherwise mentioned, chemicals were purchased from Aldrich, USA. Irgacure 2959 was obtained from CIBA. Polyethersulfone (PES) membranes were obtained from GE Water (5 micron pore size; 150 micron thickness). PE sheets (bags) were obtained from Fisher, USA (cat #19075388A).

A solution which was used for making a coating on the membrane is described here as a coating-solution. The membrane was soaked in a coating-solution for 1 min or in some examples for 20 min The excess coating-solution was removed by placing the membrane between two polyethylene (PE) sheets and using a silicone blade to squeeze out the excess solution, followed by air-drying for about 45-70 min The membrane was mounted on a frame and was placed into the e-beam chamber. $N_2$ was purged through the chamber for 2 min, and the membrane was exposed to an electron beam at a rate of 50 feet per min A dose of 40 KGy was delivered when the $O_2$ level reached 150 ppm (+/−5). The membrane was turned over and the exposure procedure was repeated for the other surface of the membrane (Bench Top Electron Beam Unit, EB Lab-150, ~40 cm square chamber, AEB, Wilmington, Mass.).

In one example, (Prototype 1) a polyethersulfone membrane (5 micron, from GE Water) was coated with an aqueous formulation (coating-solution) comprising 10 g vinylbenzyltrimethylammonium chloride (0.047 mol), 8 g diallyldimethylammonium chloride (0.050 mol), 3 g methylenebisacrylamide (0.020 mol), and 1.0 g Irgacure 2959 (0.0045 mol) in 200 ml of water. The membrane was immersed in the coating-solution for 20 min The membrane was then removed from the solution and was squeezed gently between two polyester sheets to remove air bubbles. The coating solution was driven through the membrane and the excess solution was removed from the membrane. The membrane was subsequently air dried while hanging for 60 min, before being exposed to e-beam irradiation (40 KGray) on both sides (150 ppm oxygen).

In another example, (Prototype 2) a polyethersulfone membrane (5 micron, from GE Water) was coated with a formulation (coating-solution) comprising 26.5 g vinylbenzyl[piperidineethanol]ammonium chloride (0.094 mol), 1.5 g methylenebisacrylamide (0.010 mol), and 0.88 g Irgacure 2959 (0.004 mol) in 117 ml of a mixture of water and methanol (35:65) (15 wt % monomer). The membrane was immersed in the coating solution for 20 min The membrane was then removed from the solution and was squeezed gently between two polyester sheets to remove air bubbles. The coating-solution was driven through the membrane and the excess solution was removed. The membrane was subsequently air dried while hanging for 45-60 min while hanging, before being exposed to e-beam irradiation (40 KGray) on both sides (150 ppm oxygen).

In another example (Prototype 3), a polyethersulfone membrane (5 micron, from GE Water) was coated with a coating solution comprising 27.66 g vinylbenzyl(N-benzyl-N-hydroxyethyl-N-methyl)ammonium chloride (0.087 mol), 1.85 g methylenebisacrylamide (0.010 mol), and 0.88 g Irgacure 2959 (0.004 mol) in 218 ml of a mixture of water and methanol (35:65) (13 wt % monomer). The membrane coating solution was diluted with a mixture of water and methanol (35:65) (8.5 wt % monomer). The membrane was immersed in the diluted coating solution for 20 min The membrane was then removed from the solution and was squeezed gently between two polyester sheets to remove air bubbles. The coating-solution was driven through the membrane and the excess solution was removed. The membrane was subsequently air dried for 45-60 min while hanging, before being exposed to e-beam irradiation (40 KGray) on both sides (150 ppm oxygen).

In yet another example, (Prototype 4) a polyethersulfone membrane (5 micron, from GE Water) was coated with an aqueous/methanol formulation containing 30.0 g vinylbenzyl (N-benzyl-N-hydroxyethyl-N-methyl)ammonium chloride (0.09 mol), 2.727 g N-(hydroxymethyl)acrylamide (0.027M, as a 48 wt % solution in water, 5.687 g solution), 4.1487 g methylenebisacrylamide (0.0269 mol), and 2.0 g Irgacure 2959 (0.009 mol) in a mixture of 215 ml of water and 209 ml of methanol (7.66 wt % monomer in ~50/50 water:methanol). The membrane was immersed in the coating-solution for 1 min, and the solution was removed and squeezed gently between two polyester sheets to remove air bubbles. The coating solution was then driven through the membrane and excess solution was removed. The membrane was subsequently air dried horizontally for 2 min then dried for 58 min on a polyester sheet, before being exposed to e-beam irradiation (40 KGray) on both sides (150 ppm oxygen).

Example 3

Membrane Flux and Permeability

Membrane flux and permeability of a single layer of membrane was determined using two buffers and de-ionized (DI) water. The time required for 10 ml of Tris buffer (25 mM) with 100 mM NaCl to flow through a single layer of membrane was determined at a set level of pressure. The single layer of membrane was held in a 25 mm glass filter holder (Millipore) and the vacuum was typically set at 27" Hg or 5" mm of Hg. Times were also measured for 70 mM phosphate buffer at pH 6.5 and DI water. A needle gauge was used to regulate the vacuum (Glass Filter holder, 25 mm with stainless steel support, Millipore Corp XX10 025 30; Needle gauge, Cole-Parmer Instrument Corp, K-06393-61, Vacuum gauge, Ashcroft Corp, 238A 460-02).

Example 4

BSA Assay Method

All buffers were stored at room temperature. Buffers were degassed under vacuum for at least 5 minutes with continual mixing.

High conductivity Buffer A is a 25 mM Tris buffer, pH 8.0 with 100 mM NaCl. The buffer comprises 25 ml 1 M Tris, 15 ml 5 M Sodium Chloride; and water (to a final volume of 1 L). The buffer was filtered, degassed and the conductivity was measured before use. Conductivity of this Buffer A was recorded as 12-13 mS/cm. Low Conductivity Buffer A is a Tris buffer; 25 mM Tris, pH 8.0 containing 15 mM NaCl. The buffer comprises 25 ml of 1 M Tris, pH 8.0; 3 ml of 5 M Sodium Chloride; and water (to a final volume of 1 L). The buffer was filtered, degassed and the conductivity was measured before use. Conductivity of this buffer A was recorded as 3.1-3.2 mS/cm.

Buffer B is a Strip buffer (100 mM Sodium Phosphate, pH 3.0). Buffer B comprises 0.698 ml phosphoric acid; 12.371 g $NaH_2PO_4$; and water (to a final volume of 1 L). The buffer was filtered and degassed prior to use. Conductivity of the buffer B was recorded as 7-8 mS/cm.

Stock solutions for phosphate buffers were prepared as follows: 0.5 M solution of sodium phosphate monobasic (FW=119.96) was made by dissolving 59.98 g sodium phosphate monobasic in a final volume of 1 L of water. 0.5 M solution of sodium phosphate dibasic (FW=141.96) was prepared by dissolving 70.98 g sodium phosphate dibasic in a final volume of 1 L of water. A stock of 0.5 M sodium phosphate buffer was prepared by mixing 0.5 M sodium phosphate monobasic and 0.5 M sodium phosphate dibasic while stirring and monitoring until the desired pH was reached. The stock buffer was diluted as appropriate to reach the desired concentration and salt was added as necessary to reach the desired conductivity. Sodium phosphate buffer, pH 6.5 is a 50 mM sodium phosphate buffer, pH 6.5 containing 35 mM NaCl made by mixing 100 ml 0.5 M Sodium phosphate buffer, pH 6.5 and 7 ml 5 M NaCl in water to a final volume of 1 L. The buffer was filtered, degassed and the conductivity was measured before use. Conductivity of the buffer was recorded as ~8 mS/cm. Sodium phosphate, pH 7.4 is a 50 mM sodium phosphate buffer, pH 7.4 containing 10 mM NaCl was made by mixing 100 ml sodium phosphate buffer, pH 7.4 and 2 ml 5 M NaCl in water to a final volume of 1 L. The buffer was filtered, degassed and the conductivity was measured before use. Conductivity of the buffer was recorded as: ~7.2 mS/cm.

0.5 N NaOH solution was made by adding 40 ml concentrated stock of sodium hydroxide (12.5 N) to 960 ml water. The solution was filtered and degassed before use.

A stock of BSA was prepared in the desired Buffer A at a concentration of about 6 mg/ml. The stock was filtered, degassed and the absorbance was determined at 280 nm using a spectrophotometer to ascertain the actual protein concentration after filtering. This concentrated stock was stored at 4° C. in the dark. The concentrated stock was diluted with the same Buffer A to achieve working concentrations ranging from 0.025 mg/ml to 1.0 mg/ml. The diluted working solution was stored at 4° C. in the dark. The solution was allowed to warm at room temperature (in the dark) and the concentration was measured using a spectrophotometer before use.

The chromatographic assay using BSA was carried out as described below. The chromatographic device was equilibrated by 15 ml Buffer A. 10 ml of BSA solution (0.025 mg/ml to 1 mg/ml concentration) was injected to the device. 15 ml Buffer A was passed through the device to wash out the unbound sample followed by 100% Buffer B (15 ml). The device was further washed with 10 ml of 0.5 N NaOH, and finally re-equilibrated with 15 ml Buffer A. Binding capacity for matrix present in the chromatographic device was determined at 10% breakthrough (also referred to as QB10 value) at 280 nm (Bo-Lennart Johansson et al. J. Chromatogr. A 1016 (2003) 21-33) using an Akta Explorer instrument (GE Healthcare).

Dynamic BSA Binding Capacity (mg Protein Per ml of Membrane Volume)

TABLE 2

| Set | Flux LMH/PSI Phosphate Buffer pH 6.5 | Ligand Density (mol/ml) QB50 | BSA (mg/ml) Tris pH 8 3 mS/cm | BSA (mg/ml) Tris pH 8 12 mS/cm | BSA (mg/ml) Phosphate pH 6.5 7-8 mS/cm | BSA (mg/ml) Phosphate pH 7.5 7-8 mS/cm |
|---|---|---|---|---|---|---|
| 1 | 1121 | ND | 20 | ND | 1 | ND |
| 2 | 859 | ND | ND | ND | 4 | 16 |
| 3 | 1252 | 20 | ND | ND | 6 | 16 |
| 4 | 3400 | 80-90 | 8 | 9 | ND | 12 |
| 5 | 4000 | 180 | 20 | 8 | 2 | 2 |

QB50 = 50% breakthrough. ND = not determined; Flux LMH/PSI ([Liters per meter squared per hour]/[pound per square inch]).

Table 2 shows better binding capacity of BSA by using the matrix of present invention. In set 5, a commercially available quaternary ammonium adsorber membrane (Q adsorber membrane manufactured by Sartorius) was used. As shown in Table 2, Sets 2, 3, and 4 show better binding capacity in phosphate buffer at pH 7.5 than a commercial Q adsorber membrane (set 5) manufactured by Sartorius. These results validate effectiveness of ligand to bind protein at 7-8 mS/cm. Sets 2, and 3 show better binding capacity in phosphate buffer at pH 6.5 than a commercial Q adsorber (set 5). The results validate effectiveness of ligand protein interaction at 7-8 mS/cm. Similarly, binding capacity at three different sets of conditions such as, varying ionic strength, conductivity, and pH in set 4 shows the expected multimodal effect. Vinylbenzyltrimethyl Q (as used in set 1) is similar to set 5 at different ionic strength, different conductivity and different pH. In order to observe the multimodal effect as seen in set 4, the phenyl moiety may protrude towards the site for binding molecules. In other case, if the phenyl moiety is not protruded towards the binding site, the behavior may be similar to that of a conventional quaternary ammonium membrane adsorber described in set 5.

Example 5

Host Cell Protein (HCP) Clearance

Clearance of HCP is better for the matrix of the invention (set 7) than a commercial Q adsorber membrane (set 6) at 7 mS/cm even at comparatively low ligand density as shown in Table 3.

TABLE 3

| Set | Buffer | Conductivity | Ligand Density (micromol/ml) | HCP Load (ng/ml of membrane) | HCP in Flow-Through (ng/ml of membrane) | % HCP in Flow-Through |
|---|---|---|---|---|---|---|
| 6 | Tris pH 7.5 | 7 mS/cm | 160 | 56.3E3 | 36.8E3 | 65 |
| 7 | Tris pH 7.5 | 7 mS/cm | 20 | 26.7E3 | 15.8E3 | 55 |

Example 6

Aggregated Antibody (mAb) Clearance

The mAb feed (mAb conc=6.4 mg/ml) contained approximately 2% mAb aggregate after purification by protein A chromatography, but prior to polishing. After polishing in flow-through (FT) mode (residence time=5 seconds) with the membrane used in Set 8 (flow rate 1.3 ml/min), the HCP content in the mAb feed was reduced from 30.9E3 ng/ml to 9.0E3 ng/ml (as shown in Table 4) of membrane (29% in FT) with 1.70% mAb aggregate. In comparison, after purification in flow-through mode with a membrane used in Set 9, a commercial Q adsorber membrane (1.65 ml/min flow rate), the HCP content is reduced from 30.9E3 ng/ml to 8.8E3 ng/ml of membrane (28% in FT) with 2% mAb aggregate. Under these conditions (1000 mg mAb/ml of membrane mAb load; Tris pH 7.5, 7 mS/cm), both membranes remove the same amount of HCP as assessed by an ELISA assay, but the multimodal adsorber membrane (as shown in Set 8) surprisingly reduces mAb aggregate by approximately 15% as assessed by size exclusion chromatography where as the commercial Q adsorber (as in Set 9) has no effect on mAb aggregate level.

TABLE 4

| Set | Buffer | Conductivity | Ligand Density (μmol/ml) | HCP Load (ng/ml of membrane) | HCP in Flow-Through (ng/ml of membrane) | % HCP in Flow-Through | % Aggregate in Flow-Through |
|---|---|---|---|---|---|---|---|
| 8 | Tris pH 7.5 | 7 mS/cm | 90 | 30.9E3 | 9.0E3 | 29 | 1.7 |
| 9 | Tris pH 7.5 | 7 mS/cm | 180 | 30.9E3 | 8.76E3 | 28 | 2.0 |

Example 7

Adsorber Membrane Combined with a Virus Filter

In order to demonstrate the polishing effectiveness of the multi-modal membrane adsorber as mentioned herein as "polishing membrane", the capacity ($V_{max}$ in L/m$^2$) of a commercial virus filtration membrane was determined (Millipore Viresolve NFP) with (shown in FIG. 2) and without the use of a polishing filter. The polyclonal IgG (Baxter: 5 mg/ml in PBS buffer pH 7.4, 155 mM NaCl) was flowed through the device in order to determine the virus filter capacity $V_{max}$ (L/m$^2$) using a gradual pore pluging model (ref Jonathan T. Royce, Practical Application of the Cake-Complete, Pore-Plugging Model for Sizing Normal Flow Filters *PDA J Pharm Sci Technol* September 2009 63:462-471).

Two experiments were performed (Table 5); wherein experiment 1 was only for Normal Flow Parvovirus (NFP) without a polishing membrane, and experiment 2 was NFP with a prototype device based on a multi-modal matrix of the invention (similar to Set 4 in Table 2) having a ligand density of about 24 mmol (about 22 mm diameter, and about 0.162 ml membrane volume) and used in a polishing mode of operation. The $V_{max}$ capacity of the NFP membrane with multimodal polishing membrane (experiment 2) was compared to that of a control (experiment 1) under identical conditions. The multi-modal polishing membrane showed increased capacity ($V_{max}$) of NFP by about 23 times. Enhanced capacity is observed in the configuration where the polishing membrane is juxtaposed upstream to the viral clearance membrane (as described in FIG. 2). Therefore, the above experiment clearly illustrates that the use of the polishing membrane of the present invention can effectively reduce aggregate content of the polyclonal feed entering a viral clearance membrane. This example further demonstrates that both the polishing and the viral clearance unit operations could be combined into a single unit operation as described in FIG. 2.

Figure 3:
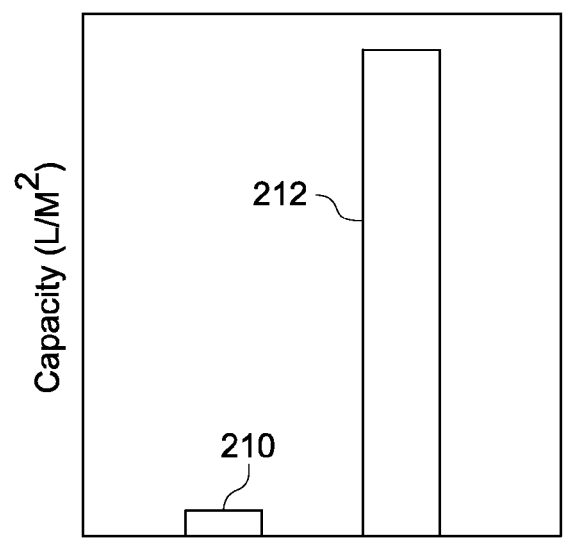
FIG. 3 shows a bar graph illustrating the capacity for virus membrane filtration wherein the virus membrane is a free standing device or incorporated in a device with a separation matrix.

FIG. 3 shows an increase in capacity of the viral clearance membrane while using a polishing membrane compared to the capacity of the viral clearance membrane without using a polishing membrane. As shown in FIG. 3 the typical capacity of a virus filter without incorporating a polishing membrane (210) is 22 litres/square meter ($L/m^2$), and the increase in capacity of the virus membrane filter with a polishing membrane juxtaposed upstream of the virus membrane filter (212) is 503 L/M2.

The results confirm the benefit of having a process in which a polishing membrane is juxtaposed upstream to a viral clearance filter, effectively providing a single unit operation.

TABLE 5

| Experiment | Conditions | Pressure (PSI) | Capacity Vmax ($L/M^2$) |
|---|---|---|---|
| 1 | NFP alone | 33 | 22 |
| 2 | Multi-modal Adsorber/NFP | 28 | 503 |

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A device for separating one or more unwanted compounds from an antibody containing biological sample, said device comprising:
    a porous support; and
    a polymeric resin disposed within the pores of the porous support wherein the polymeric resin comprises structural units derived from:
        a vinyl crosslinker; and
        an aromatic monomer comprising a quaternary ammonium group and at least two ring structures.

2. The device of claim 1, wherein the aromatic monomer having a structural unit derived from Formula I, Formula II, Formula III, or a combination thereof;

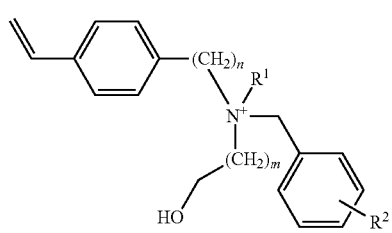
(I)

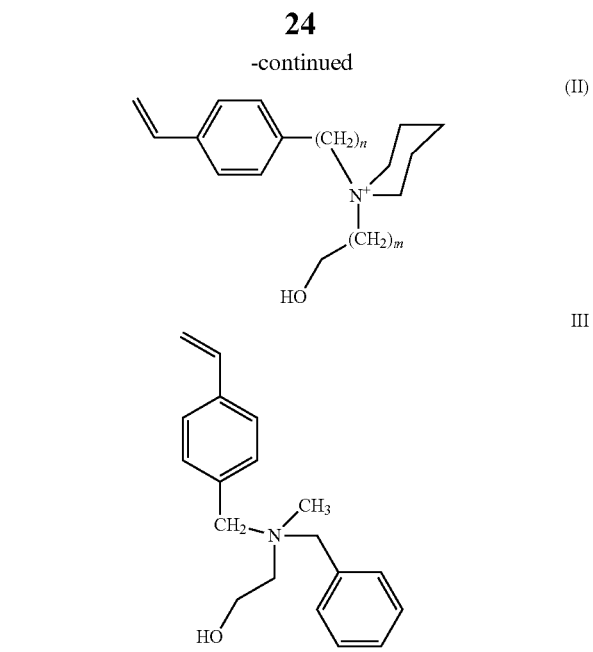

wherein $R^1$ and $R^2$ are independently a hydrogen, a $C_1$-$C_{20}$ alkyl, a $C_1$-$C_{20}$ substituted alkyl, an aryl, a substituted aryl, or a combination thereof, and m and n are independently integers between 1 and 5;
$R^3$ and $R^4$ are independently a hydrogen, a $C_1$-$C_{20}$ alkyl, a $C_1$-$C_{20}$ substituted alkyl, a benzyl or a combination thereof; and
wherein the polymeric resin is capable of selectively retaining one or more unwanted compounds present in the biological sample through a multi-modal interaction.

3. The device of claim 2, wherein $R^3$ comprises structural units derived from Formula IV

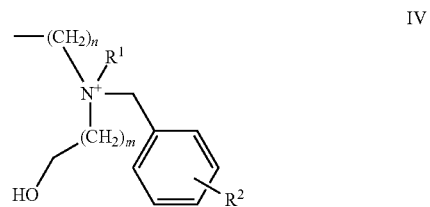
IV wherein $R^5$ and $R^6$ are independently a hydrogen, a $C_1$-$C_{20}$ alkyl, a $C_1$-$C_{20}$ substituted alkyl, an aryl, a substituted aryl, or a combination thereof, and m and n are independently integers between 1 and 5.

4. The device of claim 2, wherein the polymeric resin further comprises structural units derived from Formula V

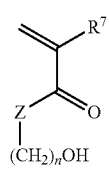
V wherein Z is NH or O;
$R^7$ is hydrogen or methyl, a $C_1$-$C_5$ alkyl, a substituted alkyl, or a combination thereof; and
n is an integer between 1 and 5.

5. The device of claim 2, wherein the vinyl crosslinker comprises N',N"-methylenebisacrylamide.

6. The device of claim 2, wherein the multi-modal interaction comprises at least two of hydrogen bonding, ionic, electrostatic, hydrophobic, Van der Waals, or dipole-dipole interactions.

7. The device of claim 2, wherein the porous support is selected from polysulfones, polyethersulfones, expanded polytetrafluoroethylene (e-PTFE), polyvinylidenefluoride (PVDF), polyphenyleneoxides, polycarbonates, polyesters, cellulose, or cellulose derivatives.

8. The device of claim 2, wherein the porous support has a pore size diameter ranging from about 0.1 microns to about 10 microns.

9. The device of claim 2, wherein the porous support has a pore size diameter ranging from about 2 microns to about 5 microns.

10. The device of claim 2, wherein the porous support is a membrane, a web, a filter, a fiber, or a mesh.

11. The device of claim 2, wherein the unwanted compounds comprise aggregated proteins or peptides, misfolded proteins or peptides, host cell proteins, nucleic acids, endotoxins, or a combination thereof.

12. The device of claim 11, wherein the aggregated proteins comprise aggregated antibodies.

13. The device of claim 2, further comprising a viral clearance membrane capable of removing virus and positioned upstream or downstream of the porous support.

14. The device of claim 13, wherein the viral clearance membrane is positioned downstream of the porous support and wherein the device is capable of improving the capacity of the viral clearance membrane by at least 10 L/m$^2$ as compared to an equivalent free standing viral clearance membrane.

15. The device of claim 14, wherein the polymeric resin further comprises structural units derived from Formula V

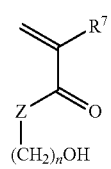

wherein Z is NH or O;

$R^7$ is hydrogen or methyl, a $C_1$-$C_5$ alkyl, a substituted alkyl, or a combination thereof; and n is an integer between 1 and 5.

16. The device of claim 2, wherein the device is in the form of a chromatographic chamber, tubular column, cartridge, syringe filter, manifold, multi-well plate, monoliths, filters, membranes, capillaries, microfluidic chips, a pleated cartridge or capsule, a cassette, a spiral filter, or a hollow fiber.

17. The device of claim 16 wherein the device is capable of being sterilized.

* * * * *